(12) United States Patent
Nakamura

(10) Patent No.: US 6,691,324 B1
(45) Date of Patent: Feb. 17, 2004

(54) SPORT PROTECTIVE HEADGEAR

(75) Inventor: Shane H. Nakamura, Vista, CA (US)

(73) Assignee: Shane Nakamura, Carlsbad, CA (US)

( * ) Notice: Subject to any disclaimer, the term of this patent is extended or adjusted under 35 U.S.C. 154(b) by 0 days.

(21) Appl. No.: 10/123,914

(22) Filed: Apr. 16, 2002

(51) Int. Cl.[7] ............................................... A63B 71/10
(52) U.S. Cl. ................................................. 2/425; 2/412
(58) Field of Search ........................... 2/425, 410, 6.3, 2/6.7, 10, 452, 411, 412, 414

(56) References Cited

U.S. PATENT DOCUMENTS

| | | | |
|---|---|---|---|
| 3,624,663 A | 11/1971 | Jones | |
| 3,691,565 A | 9/1972 | Galonek | |
| 3,897,597 A | 8/1975 | Kasper | |
| D238,120 S | 12/1975 | Rhee | |
| D243,484 S | 3/1977 | Rhee | |
| 4,847,921 A | 7/1989 | Leutholt et al. | |
| 4,912,777 A | 4/1990 | Gasbarro | |
| 5,069,205 A | 12/1991 | Urso | |
| 5,107,543 A | 4/1992 | Hansen | |
| 5,177,815 A * | 1/1993 | Andujar | 2/411 |
| 5,184,354 A | 2/1993 | Alfaro et al. | |
| 5,218,975 A | 6/1993 | Prostkoff | |
| 5,421,799 A | 6/1995 | Rabin et al. | |
| 5,481,763 A | 1/1996 | Brostrom et al. | |
| 5,636,388 A * | 6/1997 | Hodges | 2/452 |
| 5,786,932 A | 7/1998 | Pniel | |
| D402,422 S | 12/1998 | Ho | |
| D405,538 S | 2/1999 | Chih | |
| 5,915,537 A * | 6/1999 | Dallas et al. | 2/410 |
| 6,065,159 A * | 5/2000 | Hirsh | 2/425 |
| D440,652 S | 4/2001 | Pollard | |
| 6,266,827 B1 | 7/2001 | Lampe et al. | |
| 6,321,391 B1 | 11/2001 | Basso | |
| 6,325,507 B1 | 12/2001 | Jannard et al. | |
| 6,427,253 B1 * | 8/2002 | Penny | 2/412 |

FOREIGN PATENT DOCUMENTS

| | | | |
|---|---|---|---|
| DE | 3005133 A1 * | 8/1981 | |
| DE | 3129199 A1 * | 2/1983 | A42B/03/02 |

* cited by examiner

Primary Examiner—Rodney M. Lindsey
(74) Attorney, Agent, or Firm—William B. Walker (57) ABSTRACT

A goggle retention system which also acts as a sport protective headgear. The headgear takes the form of a main section which is to be placed on the occiput of a head from which extends a parietal section which is to be placed against the parietal of a head, Also, integrally connected to the main section is a right side section which is to be placed against the right side of a head and a left side section which is to be located against the left side of a head. The entire headgear is designed to retain goggles and be shock absorbing in order to protect the head of the wearer from shock that might occur during an athlete having a falling accident.

4 Claims, 14 Drawing Sheets

SPORT PROTECTIVE HEADGEAR

BACKGROUND OF THE INVENTION

1. Field of the Invention

The field of this invention relates generally to goggle retention and protective headgear for athletics and more particularly relates to a sport protective headgear that is designed primarily to be used by snowboarders and skiers.

2. Description of the Related Art

Participants in many sports use protective headgear. Football players have long worn helmets to protect themselves from blows to the head. Hockey players also wear helmets for the same reason. Bicyclists are now wearing helmets.

A relatively new sport is snowboarding which is performed on the "slopes" along with skiers. Snowboarders and skiers are especially susceptible to accidents. For the most part, these accidents involve falling. The United States Consumer Products Commission has concluded that helmet use by skiers and snowboarders could prevent or reduce the severity of forty-four percent of head injuries to adults and fifty-three percent of head injuries to children. The using of head protection by snowboarders and skiers could prevent several deaths each year. In at least one country, a national study found that head injuries amongst skiers wearing helmets were fifty percent lower than for skiers not wearing helmets.

In the past few years, more and more snowboarders and skiers are starting to wear helmets. The increase of helmet usage is great news. However, there are still a substantial number of people who refuse to wear helmets. Some snowboarders and skiers feel that helmets are big, heavy, bulky and ridiculous looking. A terminology "mushroom heads" is being applied to a user of a helmet. Also, the added weight of the helmet throws off the rider's center of gravity. Helmets are hot and sweaty. Many times, a skier or snowboarder can't even use goggles with a helmet because of the heat that is generated by the helmet which causes fogging up of the goggles. Many times, it is impractical to use a helmet with goggles because it is difficult to get the goggles to fit in conjunction with the helmet. There is a need to construct a light weight but yet very protective form of headgear that can be used by a skier and snowboarder that looks attractive and can be purchased at a reasonable cost.

The primary areas of head injury in conjunction with skiers and snowboarders are the back of a head and the sides of a head. Therefore, it is the intention of the protective headgear of the present invention to provide for protection to exactly these areas of the head.

SUMMARY OF THE INVENTION

Sport protective headgear which utilizes a main section to be placed on the occiput of a head with the main section formed of a hard rigid shell mounted on a shock absorbing layer to be placed directly against the occiput. A parietal section is integrally connected to the hard rigid shell of the main section. The parietal section is elongated and designed to be placed against the parietal of the head. The protective headgear also includes a right side section and a left side section with the right side section to be located against the right side of the head and the left side section to be located against the left side of the head.

A further embodiment of the present invention is where the basic embodiment is modified by the main section including ventilation holes to provide for the escape of heat.

A further embodiment of the present invention is where the basic embodiment is modified by the shock absorbing layer of the main section to be removable for purposes of cleaning and replacement.

A further embodiment of the present invention is where the basic embodiment is modified by the shock absorbing layer of the main section including at least one gel pack for increased shock absorbing capability.

A further embodiment of the present invention is where the basic embodiment is modified by the parietal section including an elongated slot which forms the parietal section into a bifurcated configuration defining a pair of spaced apart legs.

A further embodiment of the present invention is where the basic embodiment is modified by the both the right side section and the left side section being integral to the shock absorbing layer of the main section.

A further embodiment of the present invention is where the basic embodiment is modified by the right side section and the left side section each including at least one shock absorbing gel pad.

A further embodiment of the present invention is where the basic embodiment is modified by the right side section being a mirror image of the left side section.

A further embodiment of the present invention is where the basic embodiment is modified by the attaching of a resilient shock absorbing plate on the exterior surface of the hard rigid shell of the main section.

A further embodiment of the present invention is where the basic embodiment is modified by there being included an additional layer of shock absorbing material located between the shock absorbing plate and the hard rigid shell.

A further embodiment of the present invention is where the just previous embodiment is modified by the shock absorbing plate being disengageable relative to the hard rigid shell of the main section in order to permit the insertion of a goggle strap located between the plate and the additional layer of shock absorbing material.

A further embodiment of the present invention is where the just previous embodiment is modified by a pair of goggles being connectable between the right side section and the left side section.

DETAILED DESCRIPTION OF THE INVENTION

For a better understanding of the present invention, reference is to be made to the accompanying drawings. It is to be understood that the present invention is not limited to the precise arrangement shown in the drawings.

Figure 1:
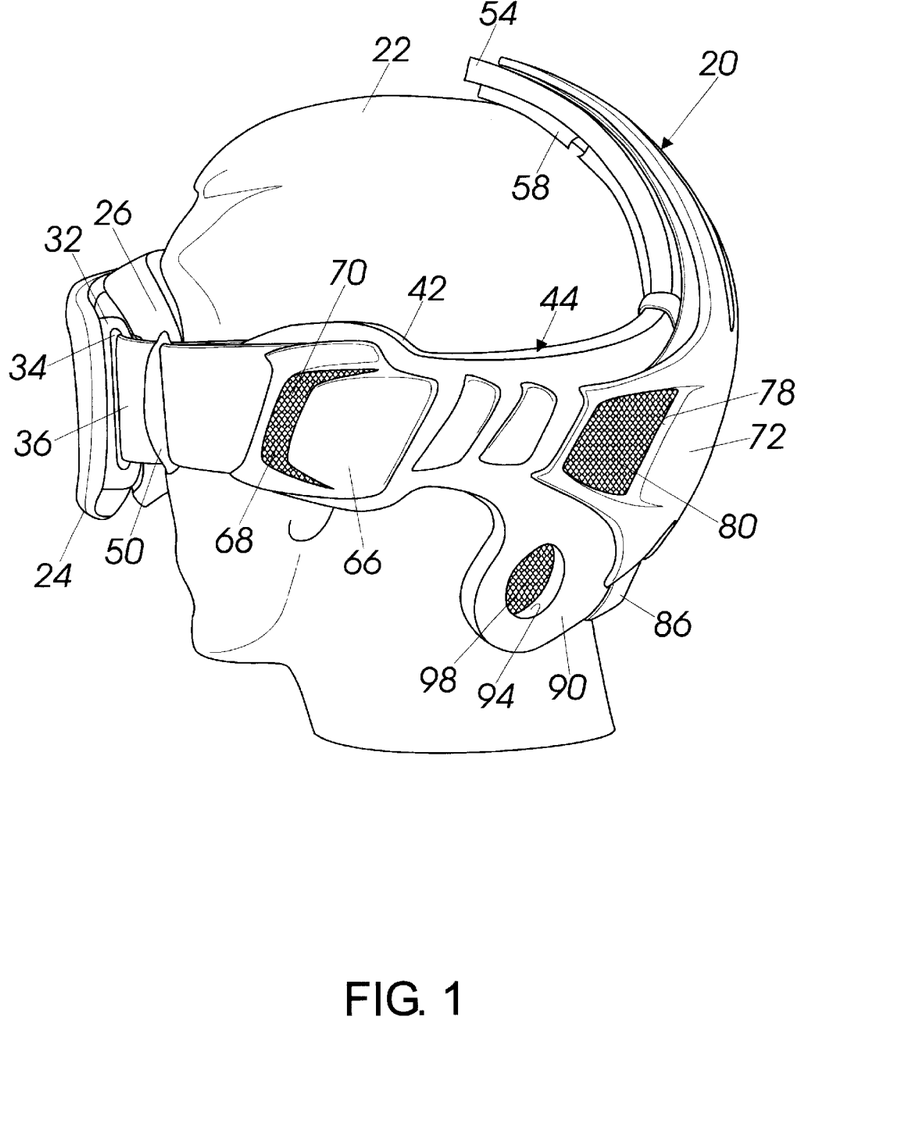
FIG. 1 is an isometric view of the first embodiment of sport protective headgear of the present invention showing such installed on a user's hea.

Referring particularly to FIGS. 1–6 of the drawings, there is shown the first embodiment 20 of sport protective headgear of the present invention. Referring particularly to FIG. 1, the sport protective headgear 20 is shown mounted on the head 22 of a human. The first embodiment 20 includes goggles 24. The goggles 24 are to be placed over the eyes of the human. Soft pad 26 of the goggles 24 is to abut directly against the face of the human 22 about the eyes. The goggles 26 includes a double pane see-through lens 28.

Mounted on the right side of the goggles 24 is a buckle bar 30. A similar buckle bar 32 is mounted on the left side of the goggles 24. Both the buckle bars 30 and 32 have an elongated slot, such as elongated slot 34 shown in buckle bar 32. A strap 36 is conducted through the elongated slot 34. A similar strap 38 is conducted through the elongated slot 34 (not shown) of the buckle bar 30. The inner end of the strap 30 is sewn on itself forming a loop. The inner end of the strap 38 is also sewn upon itself also forming a loop. The outer end of the strap 36 is conducted through slot opening 40 formed within left side extension 42 of a rigid base frame 44. In a similar manner, the free outer end of the strap 38 is conducted through a slot opening 46 formed within the right side extension 48 of the base frame 44. The outer free end of the strap 36 is connected to a buckle frame 50. The buckle frame 50 permits adjustment of the length of the strap 36 so as to tighten or loosen the goggles 24 on the head 22 of the human. Similarly, the outer free end of the strap 38 is connected to a buckle frame 52 to again provide adjustment of the goggles 24.

The left side extension 42 and the right side extension 48 are joined at the back of the base frame 44. Extending from the back of the base frame in an upward direction is a rigid parietal extension 54. Parietal extension 54 has an inner surface upon which is mounted oval-shaped resilient pads 56 and 58 and a portion of an inner liner 60 which is pretty much mounted across almost the entire surface of the base frame 44. Fixedly mounted on the inner surface base frame 44 and directly adjacent the inner liner 60 are a pair of resilient pads 62 and 64. There may also be mounted gel pads in conjunction with the back cover 72, left side extension 42 and right side extension 48. A gel pad is to be mounted interiorly of the left side cover 66, right side cover 67 and back cover 72. The purpose of the gel pads is to absorb shock upon the first embodiment 20 encountering a hard structure, such as the ground when falling. Directly adjacent the left side cover 66 is a ventilation opening 68. Mounted across opening 68 would normally be some form of a netting 70. There will be a similar ventilation opening and netting formed within the right side extension 48, which is not shown.

Figure 2:
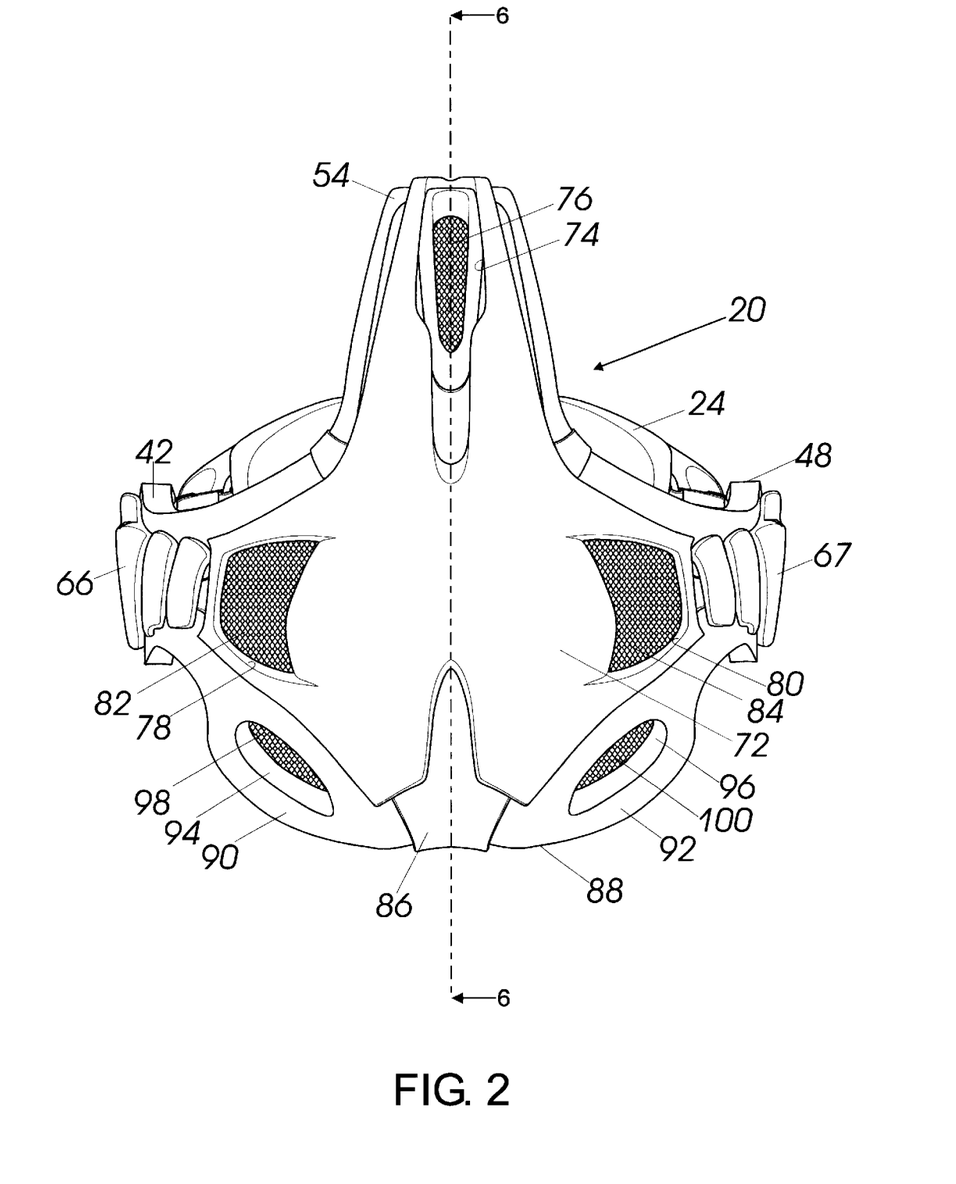
FIG. 2 is a back view of the first embodiment of sport protective headgear of the present invention.
Figure 6:
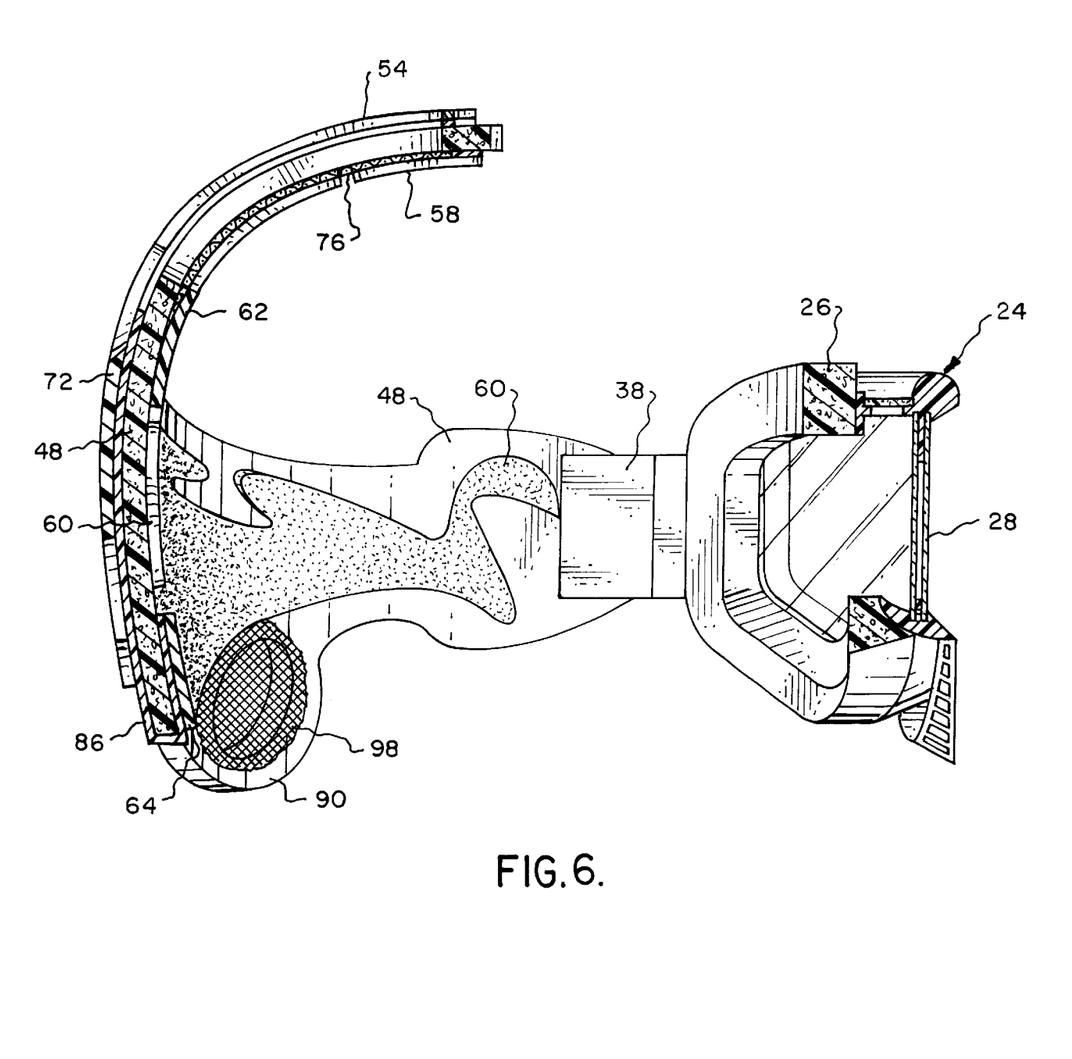
FIG. 6 is a longitudinal cross-sectional view through the first embodiment of sport protective headgear of the present invention taken along line 6—6 of FIG. 2.

Mounted across the back of the first embodiment 20 is the back cover 72. The back cover 72 will extend up across the exterior surface of the parietal extension 54. The back cover 72 includes an elongated ventilation opening 74 which again will normally be closed by a netting 76. It is to be understood that the netting 76, as well as netting 70, will easily permit the passage of air therethrough for purposes of ventilation. The ventilation openings that are provided with the first embodiment 20 are to help keep the head 22 of the wearer cool. It is to be noted that the inner liner 60 will extend and pretty much cover the inside surface of the left side extension 42 and the right side extension 48. It is also to be understood that the inner liner 60 will be adhesively secured to the back area, the inside surface of the parietal extension 54, the inside surface of the left side extension 42 and the inside surface of the right side extension 48.

The back cover 72 has a left side ventilation opening 78 and a right side ventilation opening 80. The left side ventilation opening 78 includes a section of netting 82. A similar section of netting 84 covers the right side ventilation opening 80. The parietal extension 54, the left side extension 42 and the right side extension 48 as well as the back portion will normally be constructed of a shock absorbing material. A slightly deflectable foam, rubber or plastic material will be preferred. The back cover 72 will be adhesively mounted on the exterior surface of the structure that makes up the left side extension 42, the right side extension 48 and parietal extension 54. The back cover 72 will normally be constructed of a hard plastic material. In between the inner surface of the back cover 72 and the back of the first embodiment 20 is a shock absorbing pad 86. Pad 86 normally will be constructed of a layer of fabric or rubber material. Pad 86 is to extend to be in alignment with neck edge 88.

Figure 5:
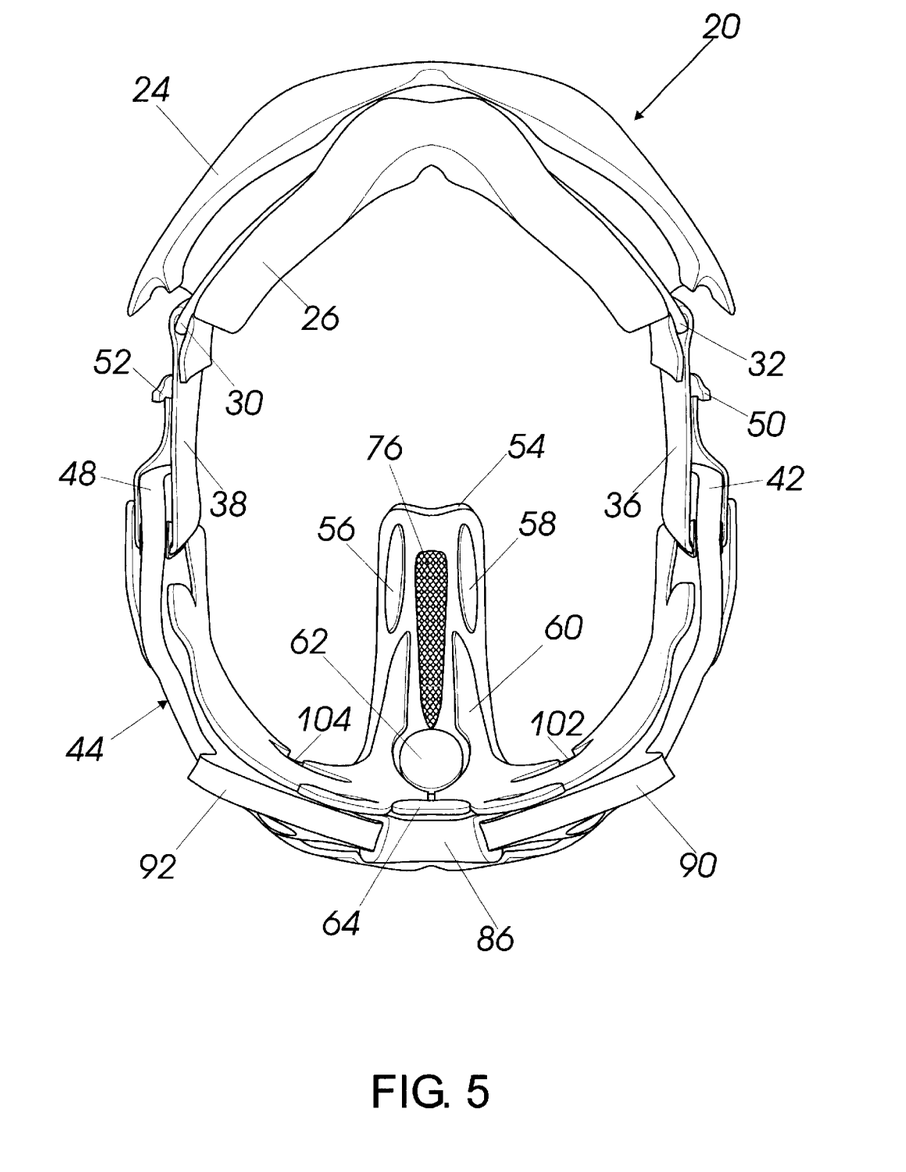
FIG. 5 is a bottom plan view of the first embodiment of sport protective headgear of the present invention.

The back of the first embodiment 20 that is connected to the left side extension 42, the right side extension 48 and the parietal section 54 also includes left side neck extension 90 and right side neck extension 92. The neck extensions 90 and 92 will be located directly adjacent the neck of the wearer and function to retain the headgear in place. The left side neck extension 90 includes a ventilation opening 94. Similarly, the right side neck extension 92 includes a ventilation opening 96. The openings 94 and 96 are basically mirror images of each other and about the same size. The same is also true regarding openings 78 and 80 which are also mirror images and are about the same size. Included within opening 94 is netting 98. A similar netting 100 is included within the opening 96.

The common areas of a user's head that typically encounters a striking force are the back of the head 22 and the right and left sides of the head 22. By the first embodiment 20 of this invention, the back cover 72 combined with the pad 86 and the main supporting structure on which it is mounted provides protection to the back of the head 22. The right side of the head is provided protection by left side cover 66 and right side cover 67. The parietal, or top of the head, is provided protection by the parietal extension 54.

Figure 3:
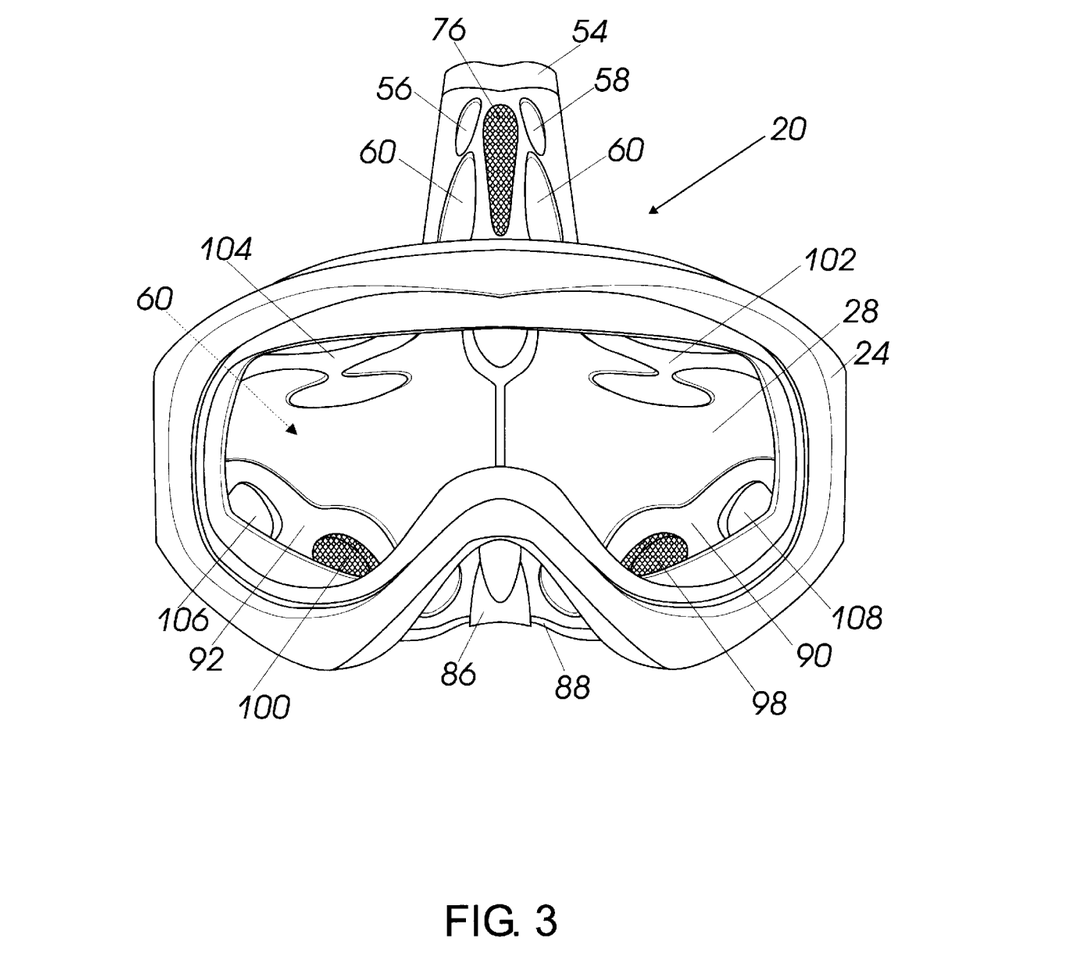
FIG. 3 is a front view of the first embodiment of sport protective headgear of the present invention.
Figure 4:
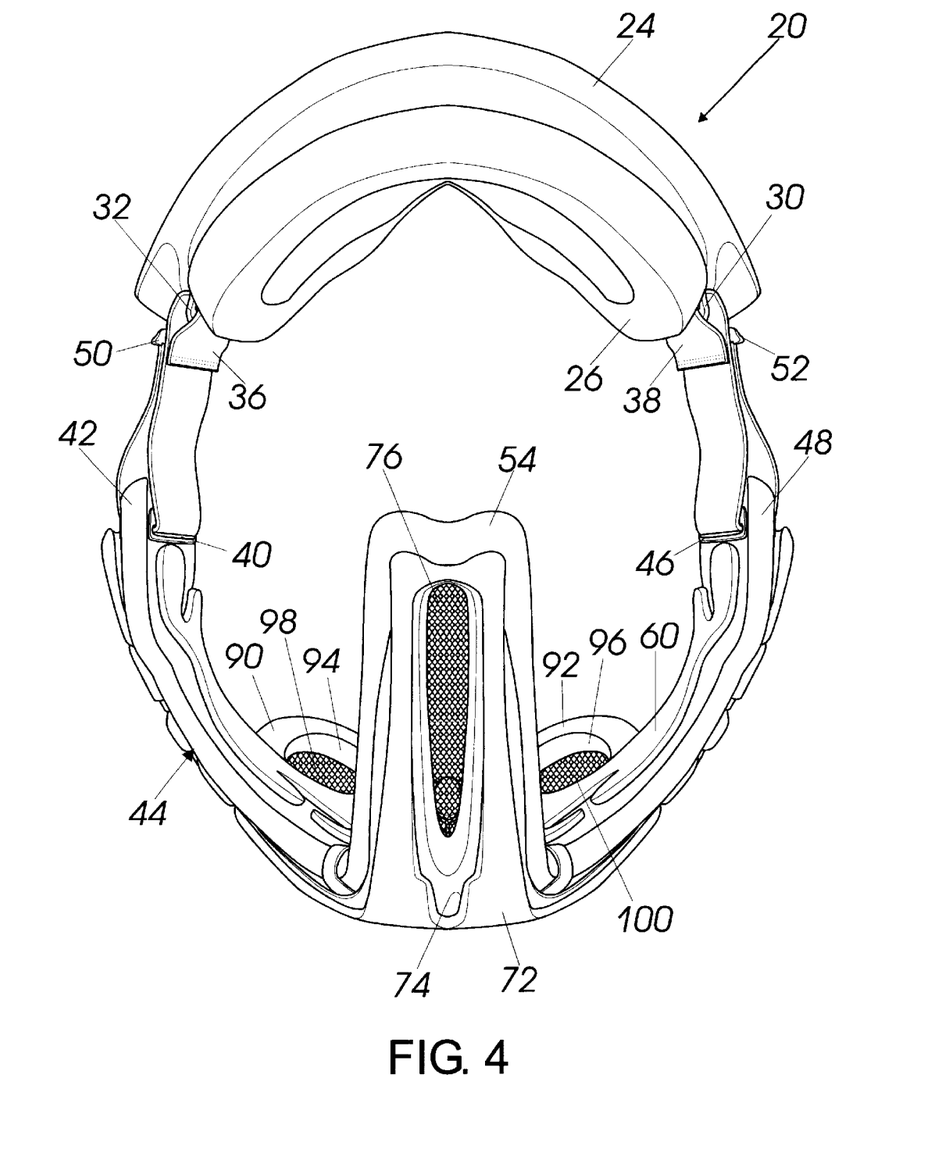
FIG. 4 is a top plan view of the first embodiment of sport protective headgear of the present invention.

The inner layer 60 includes a series of specially configured cutouts 102, 104, 106 and 108. These cutouts are mainly for purposes of ventilation and also to provide a high tech attractive appearance.

Referring particularly to FIGS. 7–14 of the drawings, there is shown the second embodiment 110 of sport protective headgear of this invention which is shown mounted on head 112 of a user. The second embodiment 110 is formed of a main frame member 114 which again will be constructed of a somewhat resilient shock absorbing material, usually rubber or plastic. The main frame member 114 includes a parietal extension 116, a right side extension 118, a left side extension 120, a right side neck extension 122 and a left side neck extension 124. The inner surface of the main frame member 114 has fixedly mounted thereon a series of resilient pads 126, 128, 130, 132, 133 and inner liner 134. The inner liner 134 extends to cover substantially most of the parietal extension 116, the right side extension 118, and the left side extension 120 as well as a portion of the right side neck extension 122 and the left side neck extension 124. It is to be understood that the adhesive liner 134 as well as resilient pads (possibly constructed of neoprene) 126, 128, 130, 132, 133 and inner liner 134 are adhesively secured to the main frame member 114. It is also to be noted that the inner liner 134 is actually composed of two separate inner liner members which include a central cut-out area 136.

Figure 11:
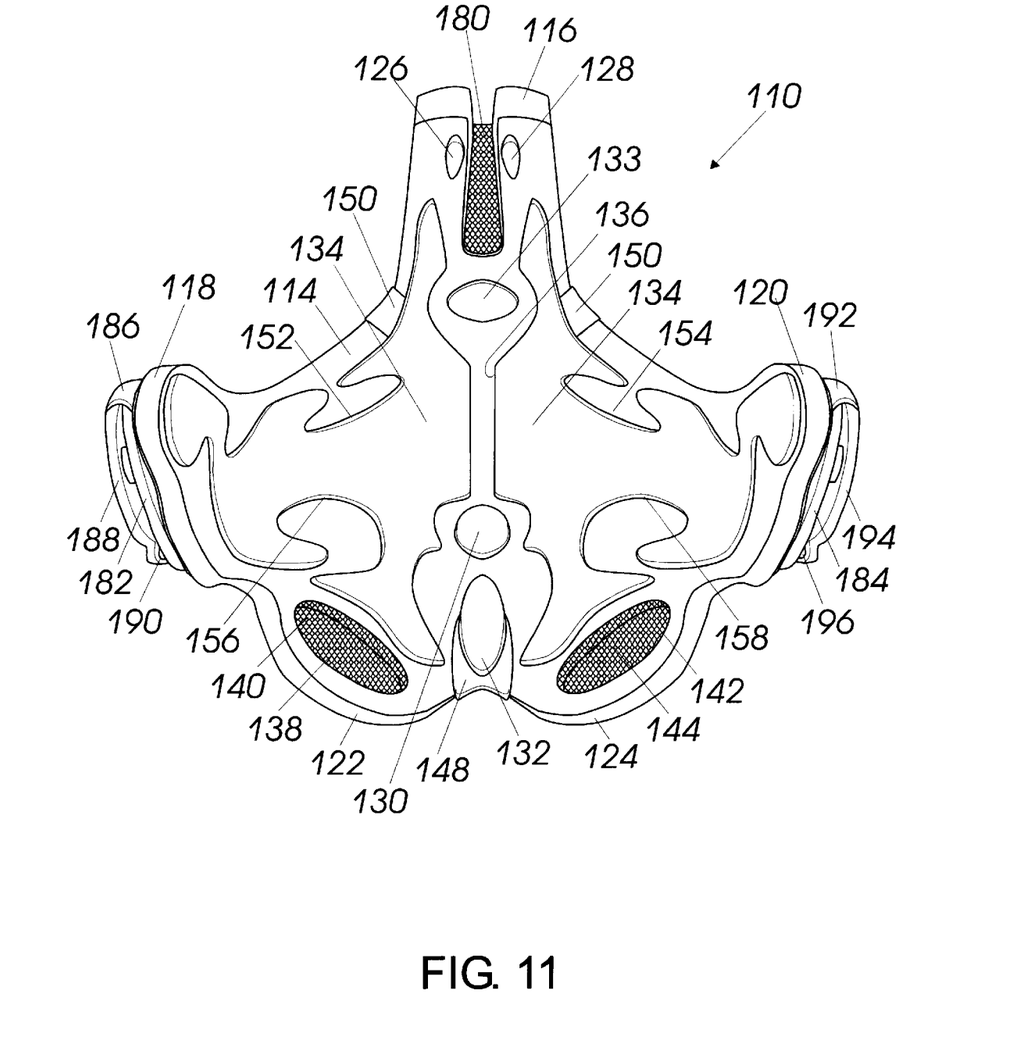
FIG. 11 is a front view of the second embodiment of sport protective headgear of the present invention.
Figure 13:
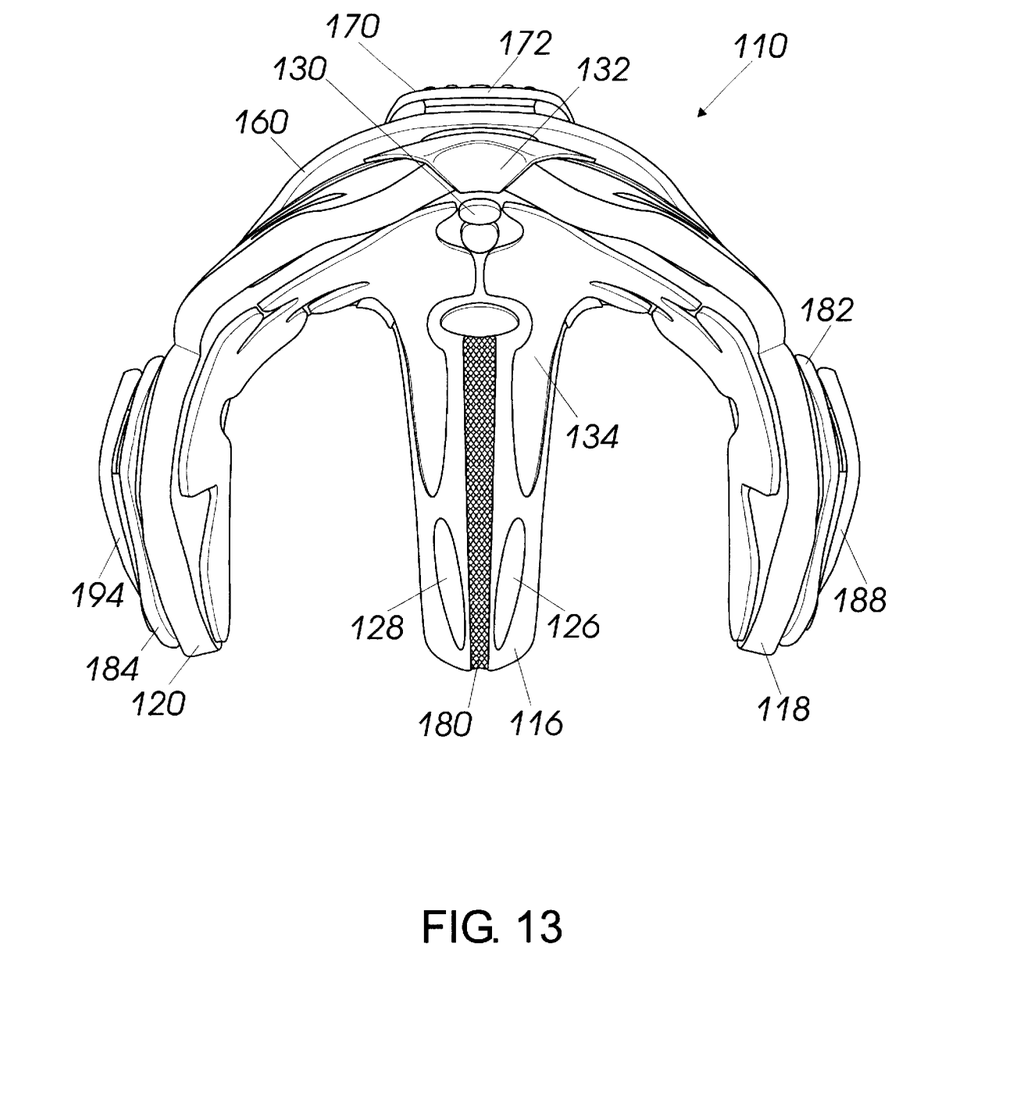
FIG. 13 is a bottom plan view of the second embodiment of sport protective headgear of the present invention.
Figure 14:
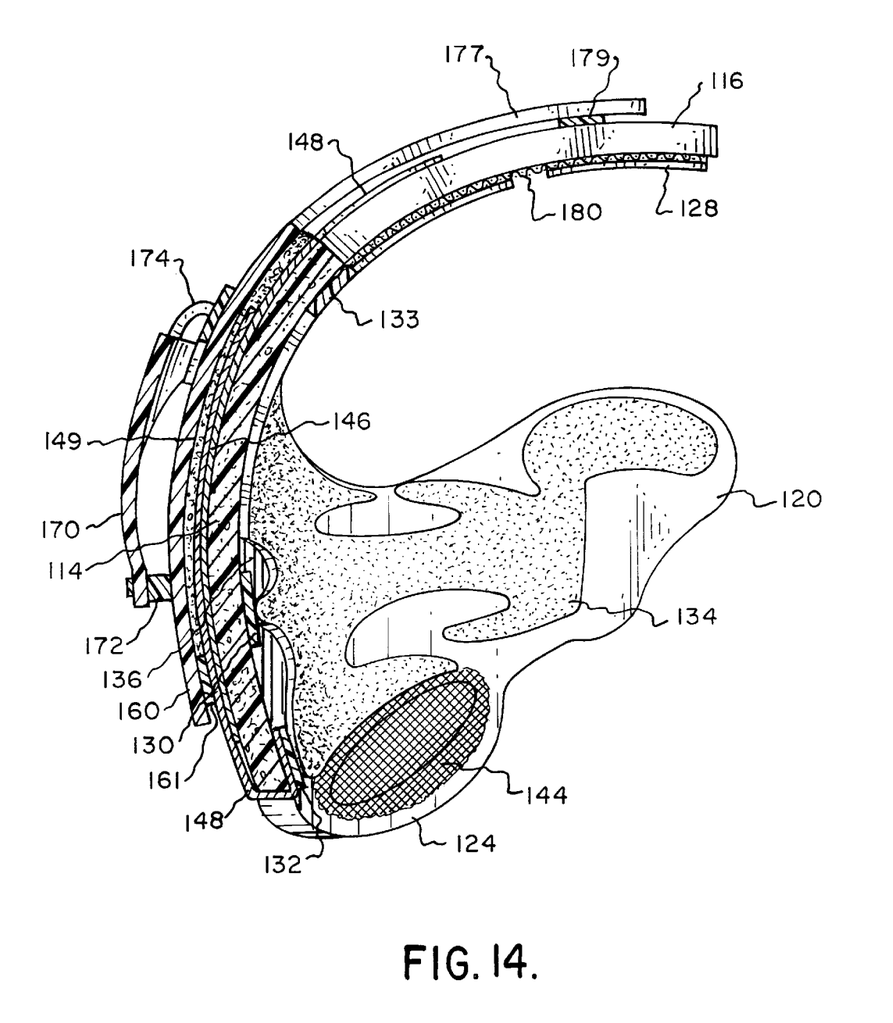
FIG. 14 is a longitudinal cross-sectional view of the second embodiment of sport protective headgear of the present invention taken along line 14—14 of FIG. 10.

The right side neck extension 122 includes a ventilation opening 138 which is covered by a netting 140. The left side neck extension 124 includes a ventilation opening 142 which is covered by a netting 144. Mounted on the exterior surface of the main frame member 114 is a fabric liner 146. Mounted about the back section of the main frame member 114 and against the fabric liner 146 is a shock absorbing pad 148 (about 0.046 inches thick). The pad 148 is helped to be retained in place by a pair of attaching straps 150 which is mounted over the peripheral edge of the main frame member 114. One of the attaching straps 150 will be on one side of the parietal extension 116 and the other strap 150 is located on the opposite side of the parietal extension 116. The inner liner 134 is to include a series of cut-outs 152, 154, 156 and 158 with these cut-outs being intended to increase flow of air for ventilation purposes.

Figure 7:
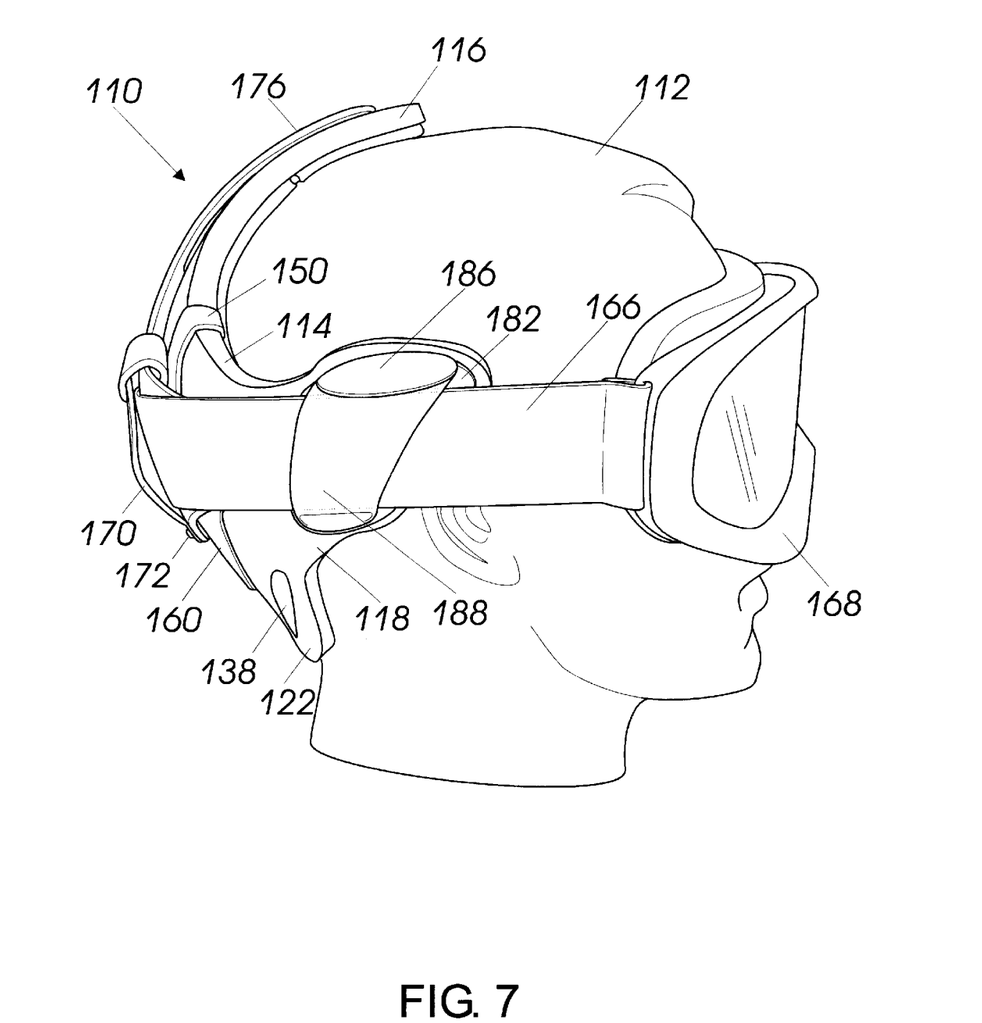
FIG. 7 is a side view of a second embodiment of sport protective headgear of the present invention showing such installed on the head of a user and with a conventional goggles being also mounted on the head of the user and connected to the headgear.
Figure 9:
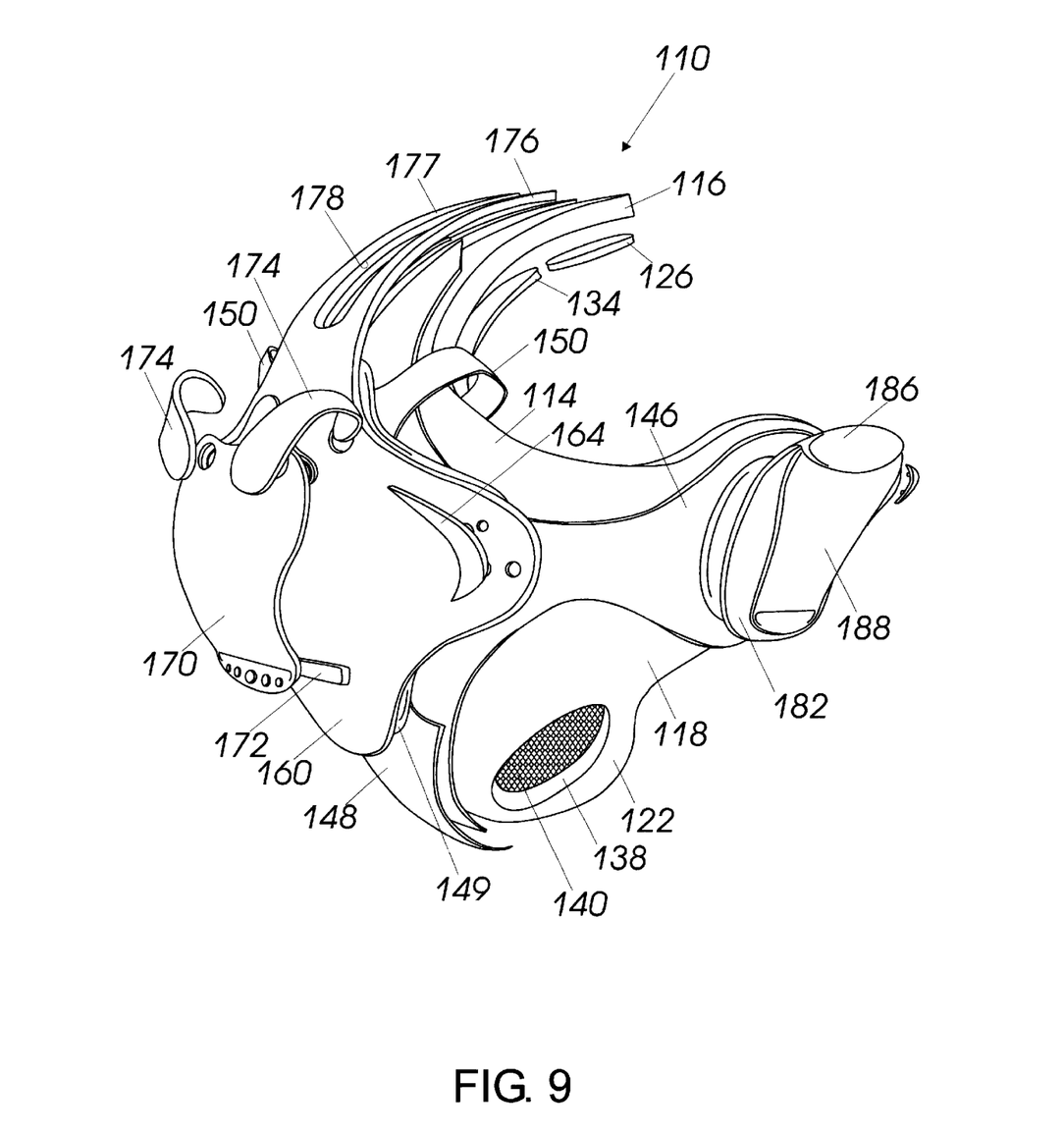
FIG. 9 is a right side/rear direction isometric view of the second embodiment of sport protective headgear of the present invention.
Figure 10:
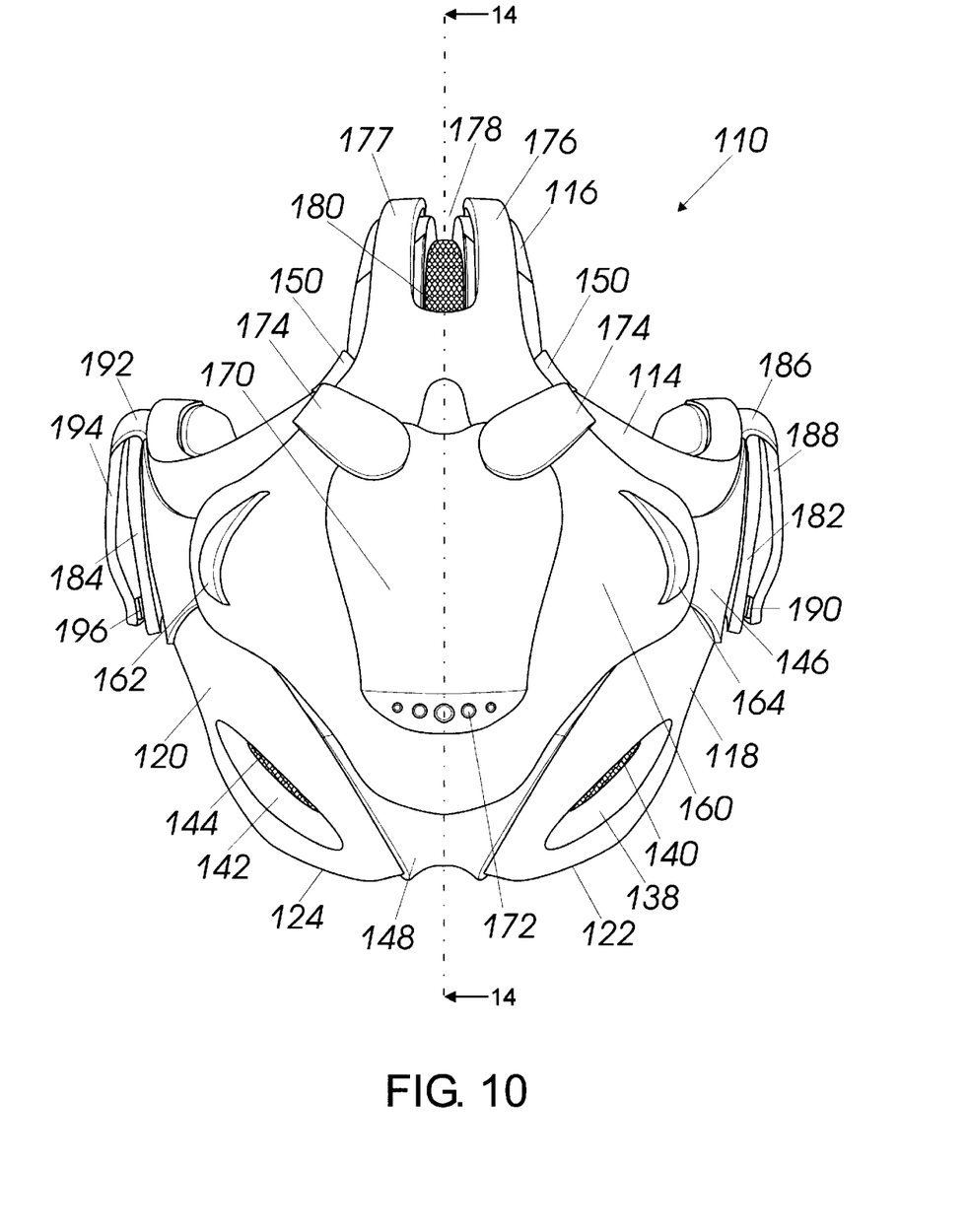
FIG. 10 is a rear view of the second embodiment of sport protective headgear of the present invention.

The lower edge of the pad 148 is wrapped around the lower edge of the main frame member 114 and connects with the resilient pad 132. Mounted on the exterior surface of the pad 148 is a gel pad 149. Outside of gel pad 149 is a rigid plastic shell 160. The rigid plastic shell 160 is to be fixedly secured to the main frame member 114. However, the shell 160 does provide a slight amount of flexibility relative to the main frame member 114 so that upon the shell 160 encountering a shocking force that the shell 160 will function to distribute that force across its entire area for that force to then be absorbed by the gel pad 149, shock absorbing pad 148, fabric liner 146 and main frame member 114. Mounted on the exterior surface of the shell 160 are grips 162 and 164. The grips 162 and 164 comprise protrusions which help to retain in place a goggle strap 166 which is connected to goggles 168 which will normally be worn in conjunction with the second embodiment 110 of this invention. The goggle strap 166 is also retained in place by a back plate 170 which is hingedly mounted by hinge 172 to the shell 160. The back plate 170 is only capable of a limited amount of the hinging movement in order to permit the goggle strap 166 to be inserted between the back plate 170 and the shell 160. When the goggle strap 166 is so inserted, securement straps 174 which are fixedly secured to the shell 160 are then to be fastened to the back plate 170.

Figure 12:
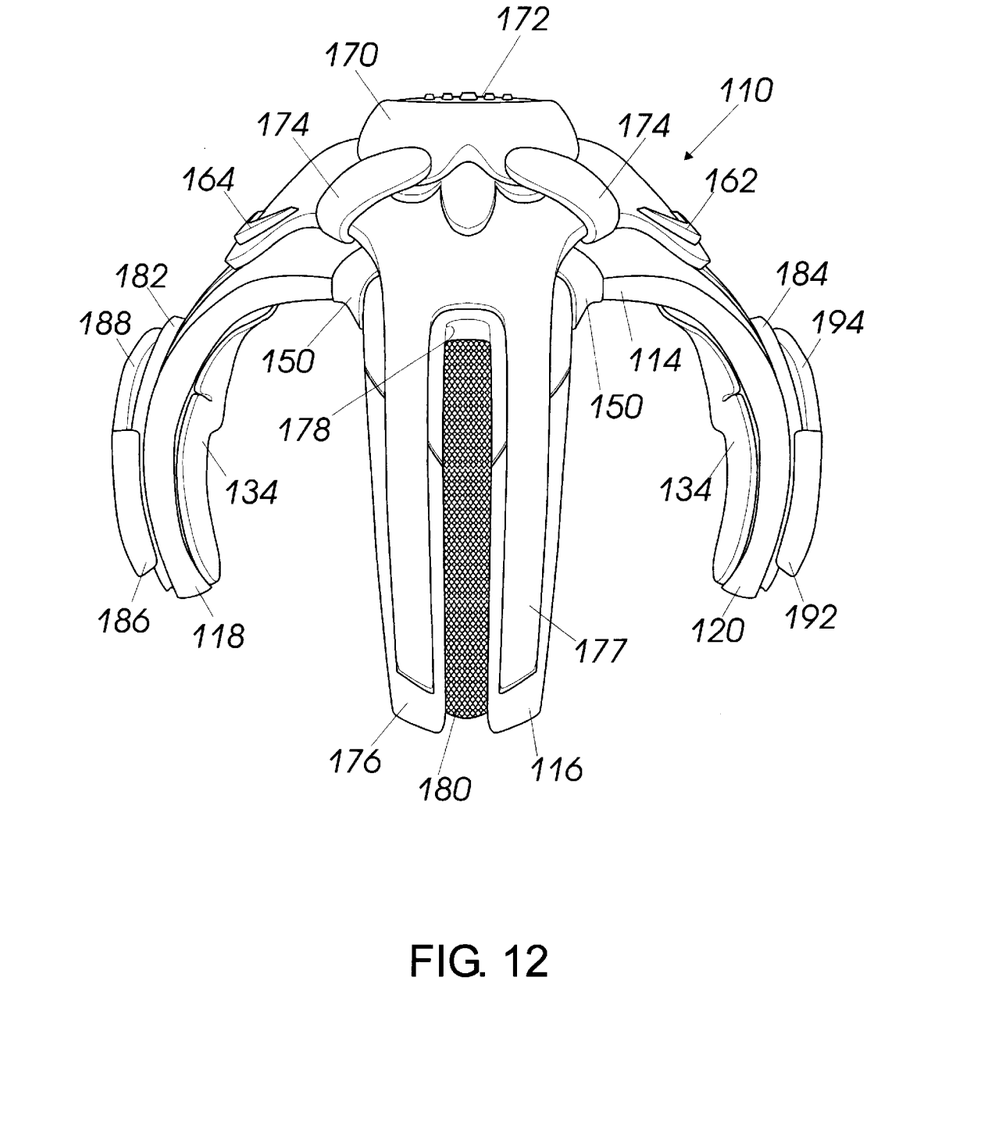
FIG. 12 is a top plan view of the second embodiment of sport protective headgear of the present invention.

The parietal extension 116 has a pair of legs 176 and 177 mounted thereon. The parietal section 176 is integral with the shell 160. The parietal section 176 has an elongated center slot 178. The center slot 178 will normally be covered by a netting 180. Legs 176 and 177 are secured by adhesive pads 179 to parietal extension 116. Shell 160 is fixed by adhesive pads 161 to fabric liner 146.

Figure 8:
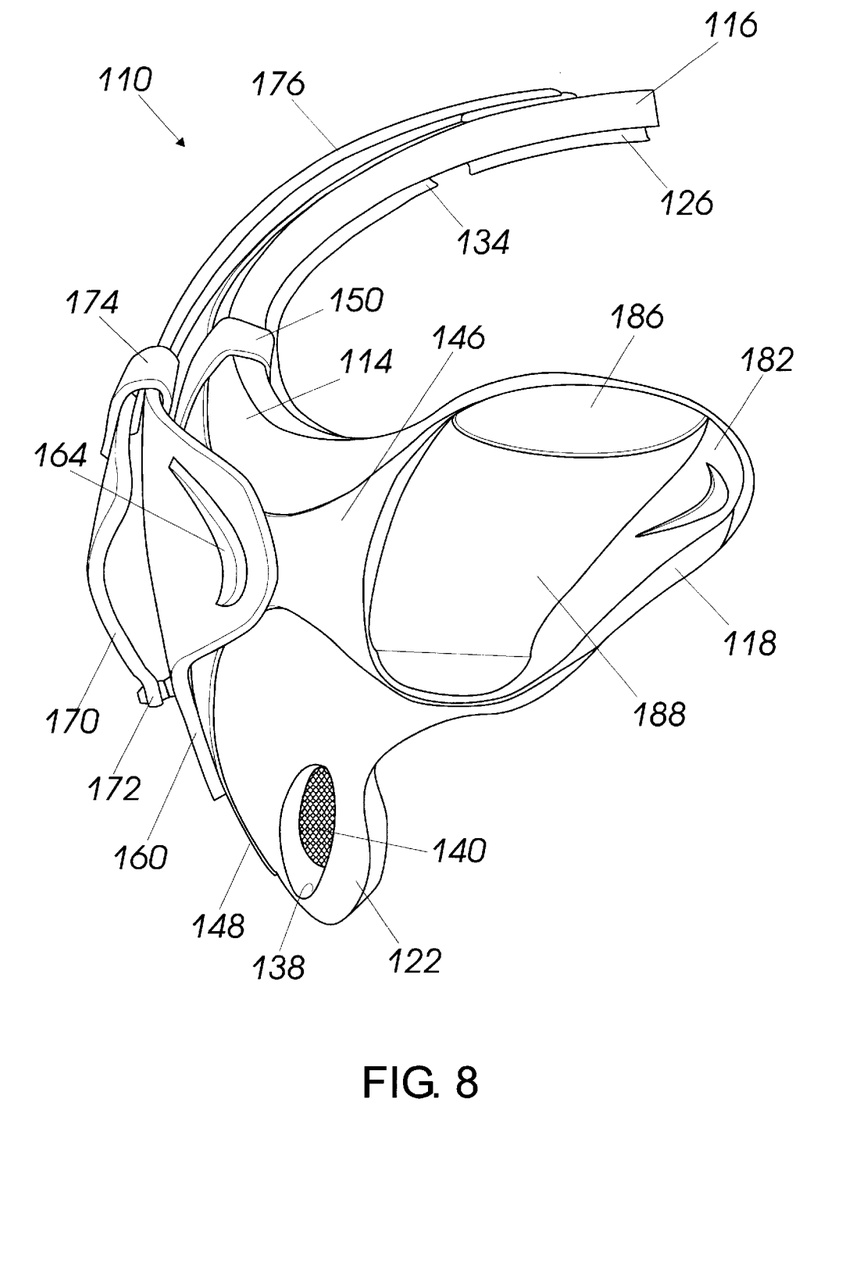
FIG. 8 is a side view similar to FIG. 7 but showing only the second embodiment of sport protective headgear of the present invention void of the goggles.

The right side extension 118 has mounted thereon an ear plate 182. A similar ear plate 184 is mounted on the left side extension 120. The ear plate 182 has hingedly mounted thereon, by means of hinge strap 186, a right side shock plate 188. The shock plate 188 is capable of pivotable movement at least ninety degrees or more relative to the ear plate 182. When in juxtaposition with the ear plate 182, there is utilized a disengageable fastener assembly 190 which retains the shock plate 188 in position relative to the ear plate 182. Similarly, hingedly mounted on the ear plate 184 a hinge strap 192 is a shock plate 194. The shock plate 194 is again pivotable by the hinge strap 192 to a position similar to how the shock plate 188 is pivotable. A fastener 196 is to be disengageably connected but is to function to secure the shock plate 194 to the ear plate 184 when the shock plate 192 is in juxtaposition with the ear plate 184. The shock plates 188 and 194 are to be pivoted outwardly away from their respective ear plates 188 and 184 in order to install in position the goggle strap 166. When the goggle strap 166 is located between the shock plate 188 and the ear plate 182 and the shock plate 194 and the ear plate 184, the shock plates 188 and 194 are reinstalled in position reengaging their respective fasteners 190 and 196.

It is the function of the shock plates 188 and 194 to absorb and distribute shock if impacted by a force to protect the sides of the head 112 of the wearer. In fact, the plates 188, 194 and 170 are located in areas where it is common that shock is encountered by the head 112 in order to distribute any shock and hopefully minimize any injury to the head 112. There may be included gel pads (not shown) in conjunction with the ear plates 184 and 188 (interiorly thereof).

The headgear of this invention may include electronics such as telecommunication equipment, storage devices and music listening devices.

What is claimed is:

1. Sport protective headgear for a human comprising:

a main section to be placed on the occiput of a head, said main section being formed of a hard rigid shell mounted on a shock absorbing layer which is to be placed against the occiput;

a parietal section integrally connected to said hard rigid shell of said main section, said parietal section being elongated and located against the parietal of a head;

a right side section connected to said main section and 10 extending from a right side edge of said main section, said right side section to be located against the right side of a head;

a left side section connected to said main section and extending from a left side edge of said main section, said left side section to be located against a left side of a head; and said parietal section being elongated and bifurcated defining an elongated slot dividing said parietal section into a pair of separate legs, each of said legs having an inherent springiness to permit deflecting of said parietal section when being installed upon a head of a human user with each of said legs exerting a slight force against the head assisting in retaining said protective headgear in position on the head.

2. Sport protective headgear for a human comprising:

a main section to be placed on the occiput of a head, said main section being formed of a hard rigid shell mounted on a shock absorbing layer which is to be placed against the occiput;

a parietal section integrally connected to said hard rigid shell of said main section, said parietal section being elongated and located against the parietal of a head;

a right side section connected to said main section and extending from a right side edge of said main section, said right side section to be located against the right side of a head;

a left side section connected to said main section and extending from a left side edge of said main section, said left side section to be located against a left side of a head;

a shock absorbing plate being mounted on said hard rigid shell and located exteriorly of said hard rigid shell, said shock absorbing plate designed to absorb shock.

3. The sport protective headgear as defined in claim 2 wherein:

there being an additional layer of shock absorbing material located between said plate and said hard rigid shell.

4. The sport protective headgear as defined in claim 3 wherein:

said shock absorbing plate being hingedly connected to said rigid shell to permit disengagement of said plate relative to said shell in order to capture a goggle strap between said plate and said additional layer of shock absorbing material.

* * * * *